United States Patent
Sakai et al.

(10) Patent No.: US 6,979,439 B1
(45) Date of Patent: Dec. 27, 2005

(54) ANTIDANDRUFF HAIR CONDITIONING COMPOSITION

(75) Inventors: Yukitoshi Sakai, Ashiya (JP); Keiichi Yasufuku, Kobe (JP); Stanley Paklap Mah, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/129,620

(22) PCT Filed: Mar. 22, 2000

(86) PCT No.: PCT/IB00/00336

§ 371 (c)(1),
(2), (4) Date: Jul. 26, 2002

(87) PCT Pub. No.: WO01/35912

PCT Pub. Date: May 25, 2001

(30) Foreign Application Priority Data

Nov. 11, 1999 (WO) ................ PCT/IB99/1815

(51) Int. Cl.⁷ .............................. A61K 7/075
(52) U.S. Cl. ................ 424/70.8; 424/70.1; 424/70.11; 424/70.12; 424/70.27
(58) Field of Search .............................. 424/70.1, 70.8, 424/70.11, 70.12, 70.27

(56) References Cited

U.S. PATENT DOCUMENTS

| | | | |
|---|---|---|---|
| 5,104,645 A | 4/1992 | Cardin et al. | |
| 5,198,209 A | 3/1993 | Zhou et al. | |
| 5,227,156 A | 7/1993 | Wiese | |
| 5,854,266 A | 12/1998 | Nelson, Jr. | |
| 6,054,450 A | 4/2000 | Shin et al. | |
| 6,468,515 B1 * | 10/2002 | Uchiyama et al. | ........ 424/70.27 |

FOREIGN PATENT DOCUMENTS

| | | |
|---|---|---|
| JP | 59108707 A | 6/1984 |
| WO | WO-96/00060 A1 | 1/1996 |
| WO | WO-97/01326 A1 | 1/1997 |
| WO | WO-98/23251 A1 | 6/1998 |
| WO | WO 99/13844 A1 | 3/1999 |

* cited by examiner

*Primary Examiner*—Jyothsna Venkat
(74) *Attorney, Agent, or Firm*—Linda M. Sivik; Tara M. Rosnell

(57) ABSTRACT

Disclosed is hair conditioning compositions comprising antidandruff agent wherein the hair conditioning composition is substantially free of the group selected from a chelating agent, methylchloroisothiazolinone, and methylisothiazolinone. The compositions comprise by weight: (a) from about 0.1% to about 15% of a high melting point fatty compound; (b) compounds selected of; (b1a) from about 0.1% to about 10% of an amidoamine having the following general formula: $R^1CONH(CH_2)_mN(R^2)_2$ wherein $R^1$ is a residue of $C_{11}$ to $C_{24}$ fatty acids, $R^2$ is a $C_1$ to $C_4$ alkyl, and m is an integer from 1 to 4; (b1b) an acid selected from the group consisting of 1 glutamic acid, lactic acid, hydrochloric acid, malic acid, acetic acid, fumaric acid, 1 glutamic acid hydrochloride, tartaric acid, and mixtures thereof, at a level such that the mole ratio of amidoamine to acid is from about 1:0.3 to about 1:1; or (b2) the combination of; (b2a) from about 0.1% to about 10% of a cationic conditioning agent; and (b2b) from about 0.1% to about 10% of a low melting point oil having a melting point of less than 25° C.; (c) a safe and effective amount of an antidandruff agent; (e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.05% to about 1.0% of mettryl paraben, and from about 0.01% to about 1.0% of propyl paraben; and (f) an aqueous carrier.

10 Claims, No Drawings

ANTIDANDRUFF HAIR CONDITIONING COMPOSITION

TECHNICAL FIELD

The present invention relates to a hair conditioning composition containing an antidandruff agent.

BACKGROUND

A variety of approaches have been developed to condition the hair. These approaches range from post-shampoo application of hair conditioners such as leave-on and rinse-off products, to hair conditioning shampoos which attempt to both clean and condition the hair from a single product.

Although some consumers prefer the ease and convenience of a shampoo which includes conditioners, a substantial proportion of consumers prefer the more conventional conditioner formulations which are applied to the hair as a separate step from shampooing, usually subsequent to shampooing. Conditioning formulations can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or amount of hair.

Antidandruff hair conditioning compositions are advantageous in that the composition is applied to the hair after the shampoo stage, thus, effective deposition on the scalp can be expected. Meanwhile, it is known that conditioning compositions containing a relatively large amount of high melting point fatty compounds, such as fatty alcohols, may grow molds under regular usage conditions unless an effective preservative system is in place. Chelating agents such as EDTA and its salts, and the agent known by tradename Kathon CG (mixture of methylchloroisothiazolinone and methylisothiazolinone) are effective preservative agents which serve this need. It has been found, however, that these specific preservative agents may interact with the antidandruff agent and thus decrease the effectiveness of the antidandruff agent and/or the preservative itself.

Based on the foregoing, there remains a desire to provide antidandruff hair conditioning compositions which provide effective antidandruff efficacy using a preservative system permitted for use in many countries, while not deteriorating conditioning benefits such as wet hair feel, spreadability, and rinsability, as well as providing glossiness, and dry combing.

None of the existing art provides all of the advantages and benefits of the present invention.

SUMMARY

The present invention is directed to a hair conditioning composition (hereafter "Hair care composition A") comprising by weight:
(a) from about 0.1% to about 15% of a high melting point fatty compound;
(b) from about 0.1% to about 10% of an amidoamine having the following general formula:

wherein $R^1$ is a residue of $C_{11}$ to $C_{24}$ fatty acids, $R^2$ is a $C_1$ to $C_4$ alkyl, and m is an integer from 1 to 4;
(c) an acid selected from the group consisting of l-glutamic acid, lactic acid, hydrochloric acid, malic acid, succinic acid, acetic acid, fumaric acid, l-glutamic acid hydrochloride, tartaric acid, and mixtures thereof, at a level such that the mole ratio of amidoamine to acid is from about 1:0.3 to about 1:1;
(d) a safe and effective amount of an antidandruff agent;
(e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben; and
(f) an aqueous carrier;
wherein the hair conditioning composition is substantially free of the group selected from a chelating agent, methylchloroisothiazolinone, and methylisothiazolinone.

The present invention is also directed to a hair conditioning composition (hereinafter "Hair care composition B") comprising by weight:
(a) from about 0.1% to about 15% of a high melting point fatty compound having a melting point of 25° C. or higher;
(b) from about 0.1% to about 10% of a cationic conditioning agent;
(c) from about 0.1% to about 10% of a low melting point oil having a melting point of less than 25° C.;
(d) a safe and effective amount of an antidandruff agent;
(e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben; and
(f) an aqueous carrier;
wherein the hair conditioning composition is substantially free of the group selected from a chelating agent, methylchloroisothiazolinone, and methylisothiazolinone.

These and other features, aspects, and advantages of the present invention will become evident to those skilled in the art from a reading of the present disclosure.

DETAILED DESCRIPTION

While the specification concludes with claims particularly pointing and distinctly claiming the invention, it is believed the present invention will be better understood from the following description.

All percentages are by weight of the total composition unless otherwise indicated. All ratios are weight ratios unless otherwise indicated. All percentages, ratios, and levels of ingredients referred to herein are based on the actual amount of the ingredient, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

High Melting Point Fatty Compound

The hair conditioning compositions A and B of the present invention comprise a high melting point fatty compound. The high melting fatty compound, together with a cationic surfactant such as an amidoamine and an aqueous carrier, provide a gel network which is suitable for providing various conditioning benefits such as slippery and slick feel on wet hair, and softness, moisturized feel, and fly-away control on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the compositions A and B at a level by weight of from about 0.1% to about 15%, preferably from about 0.25% to about 13%. More preferably, the high melting point fatty compound is included at a level by weight of from about 1% to about 10% especially in the composition A, at a level by weight of from about 0.25% to about 5% especially in the composition B.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least bout 90%, preferably at least about 95%. These single compounds of high purity provide good rinsability from the hair when the consumer rinses off the composition.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

Amidoamine

The hair conditioning composition A of the present invention comprises an amidoamine of the following general formula:

wherein $R^1$ is a residue of $C_{11}$ to $C_{24}$ fatty acids, $R^2$ is a $C_1$ to $C_4$ alkyl, and m is an integer from 1 to 4.

The amidoamine is included in the composition A at a level by weight of from about 0.1% to about 10%, preferably from about 0.25% to about 8%, more preferably from about 0.5% to about 3%.

The amidoamine can be also included in the composition B as a cationic conditioning agent at a level by weight of, preferably from about 0.1% to about 10%, more preferably from about 0.25% to about 8%, still more preferably from about 0.5% to about 3%.

Preferred amidoamines useful in the present invention includes stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof; more preferably stearamidopropyldimethylamine, stearamidoethyldiethylamine, and mixtures thereof.

Commercially available amidoamines useful herein include: stearamidopropyldimethylamine having tradename SAPDMA available from Inolex, and tradename Amidoamine MPS available from Nikko.

Acids

The hair conditioning composition A of the present invention comprises an acid selected from the group consisting of l-glutamic acid, lactic acid, hydrochloric acid, malic acid, succinic acid, acetic acid, fumaric acid, l-glutamic acid hydrochloride, tartaric acid, and mixtures thereof; preferably l-glutamic acid, lactic acid, hydrochloric acid, and mixtures thereof. The acid is contained at a level such that the mole ratio of amidoamine to acid is from about 1:0.3 to about 1:1, preferably from about 1:0.5 to about 1:0.9.

The acid can be also included in the composition B at a level such that the mole ratio of amidoamine to acid is from about 1:0.3 to about 1:1, preferably from about 1:0.5 to about 1:0.9.

Commercially available acids useful herein include: l-Glutamic acid: l-Glutamic acid (cosmetic grade) available from Ajinomoto.

Antidandruff Agent

The present compositions A and B comprise a safe and effective amount of an antidandruff agent. When present, the antidandruff agent is typically used at a level from about 0.1% to about 5%, preferably from about 0.3% to about 5%, more preferably from about 0.3% to about 1% by weight of the compositions.

Pyrithione salts are useful herein. Suitable pyrithione salts are heavy metal salts of 1-hydroxy-2-pyridinethione, the heavy metal salts being zinc, tin, cadmium, magnesium, aluminium, and zirconium. Preferred is zinc salt of 1-hydroxy-2-pyridinethione known in the art as zinc pyrithione, more preferably in a particle size of up to about 20 microns, still preferably from about 1 to about 10 microns. Commerically available pyrithione salts suitable herein include Zinc Pyrithione available from Olin.

Selenium sulfides are useful herein. Selenium sulfides herein include selenium disulfide, as well as $Se_xS_y$ in cyclic structure, wherein x and y are integers and x+y equals 8. Preferred selenium sulfides are those having a particle size of less than about 15 microns, more preferably less than about 10 microns; wherein the particle size is measured by a laser light scatterring device such as Malvern 3600 instrument.

Sulfur and octopirox, its salts, and its derivatives are also useful herein.

Antidandruff agents as mentioned above can be used alone, or in combination with one another.

Preservative System

The present compositions A and B comprise a preservative system which does not interact with the antidandruff agent, yet is effective in preventing growth of molds in the composition under regular usage and storage conditions.

The preservative system herein comprises benzyl alcohol, phenoxy ethanol, methyl paraben, and propyl paraben. The preservative system herein, as well as the conditioning composition herein, is substantially free of any chelating agents such as EDTA and its salts, and the agent known by tradename Kathon CG (mixture of methylchloroisothiazolinone and methylisothiazolinone). It has been found that, when this preservative system is used, the efficacy of the antidandruff agent is not affected, while effectiveness against mold growth is maintained, and conditioning benefit is not deteriorated. The preservative system contains, by weight of the entire compositions, typically from about 0.1% to about 1.0%, preferably from about 0.2% to about 0.6%, more preferably about 0.4% of benzyl alcohol, typically from about 0.1% to about 1.0%, preferably from about 0.2% to about 0.5%, more preferably about 0.3% of phenoxy ethanol, typically from about 0.05% to about 1.0%, preferably from about 0.1% to about 0.5%, more preferably about 0.2% of methyl paraben, and typically from about 0.01% to about 1.0% preferably from about 0.05% to about 0.5%, more preferably about 0.1% of propryl paraben. The total amount of the preservative system is such that it does not affect the rheology of the condioning compositions.

The preservative system may contain other preservatives at a safe and effective level, so long as substantially no chelating agent, methylchloroisothiazolinone, or methylisothiazolinone is included.

Aqueous Carrier

The compositions A and B of the present invention comprise an aqueous carrier. The level and species of the carrier are selected according to the compatibility with other components, and other desired characteristic of the product.

The carrier useful in the present invention include water and water solutions of lower alkyl alcohols and polyhydric alcohols. The lower alkyl alcohol useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 95%, preferably from about 30% to about 92%, and more preferably from about 50% to about 90% water.

Cationic Conditioning Agent

The hair conditioning composition B of the present invention comprises a cationic conditioning agent. This cationic conditioning agent, together with the high melting point fatty compounds, provide a gel network suitable for providing various conditioning benefits such as slippery and slick feel on wet hair, and such as softness, moisturized feel, and fly-away control on dry hair.

The cationic conditioning agent is included in the composition at a level by weight of from about 0.1% to about 10%, preferably from about 0.25% to about 8%, more preferably from about 0.5% to about 3%.

The cationic conditioning agent can be also included in the composition A at a level by weight of, preferably from about 0.1% to about 10%, more preferably from about 0.25% to about 8%, still more preferably from about 0.5% to about 3%.

The cationic conditioning agent is selected from the group consisting of cationic surfactants, cationic polymers, and mixtures thereof.

Cationic surfactant

The cationic surfactant useful herein is any known to the artisan, and can be included in the composition at a level by weight of, preferably from about 0.1% to about 10%, more preferably from about 0.25% to about 8%, still more preferably from about 0.5 to about 3%.

Among the cationic surfactants useful herein are those corresponding to the general formula (I):

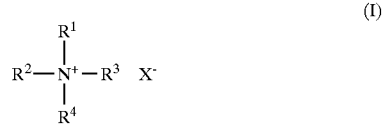

wherein at least one of $R^1$, $R^2$, $R^3$, and $R^4$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^1$, $R^2$, $R^3$, and $R^4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^1$, $R^2$, $R^3$, and $R^4$ are independently selected from $C_1$ to about $C_{22}$ alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general formula (I), preferred are those containing in the molecule at least one alkyl chain having at least 16 carbons. Nonlimiting examples of such preferred cationic surfactants include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14–18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^1$–$R^4$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VIII) below:

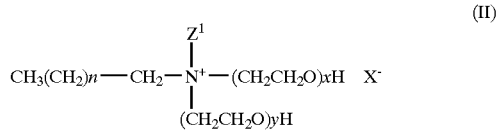

wherein n is from 8 to about 28, x+y is from 2 to about 40, $Z^1$ is a short chain alkyl, preferably a $C_1$–$C_3$ alkyl, more preferably methyl, or $(CH_2CH_2O)_zH$ wherein x+y+z is up to 60, and X is a salt forming anion as defined above;

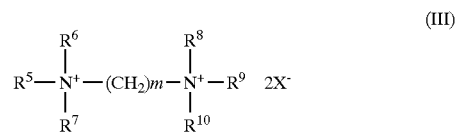

wherein m is 1 to 5, one or more of $R^5$, $R^6$, and $R^7$ are independently an $C_1$–$C_{30}$ alkyl, the remainder are $CH_2CH_2OH$, one or two of $R^8$, $R^9$, and $R^{10}$ are independently an $C_1$–$C_{30}$ alkyl, and remainder are $CH_2CH_2OH$, and X is a salt forming anion as mentioned above;

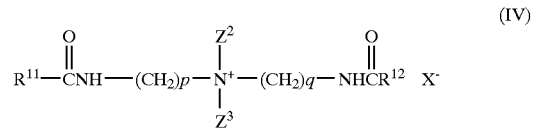

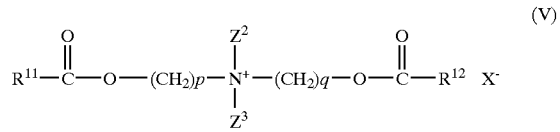

wherein, independently for formulae (IV) and (V), $Z^2$ is an alkyl, preferably a $C_1$–$C_3$ alkyl, more preferably methyl, and $Z^3$ is a short chain hydroxyalkyl, preferably hydroxymethyl or hydroxyethyl, p and q independently are integers from 2 to 4, inclusive, preferably from 2 to 3, inclusive, more preferably 2, $R^{11}$ and $R^{12}$, independently, are substituted or unsubstituted hydrocarbyls, preferably $C_{12}$–$C_{20}$ alkyl or alkenyl, and X is a salt forming anion as defined above;

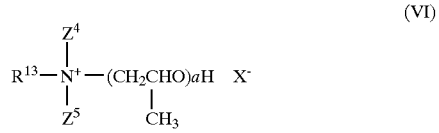

wherein $R^{13}$ is a hydrocarbyl, preferably a $C_1$–$C_3$ alkyl, more preferably methyl, $Z^4$ and $Z^5$ are, independently, short chain hydrocarbyls, preferably $C_2$–$C_4$ alkyl or alkenyl, more preferably ethyl, a is from 2 to about 40, preferably from about 7 to about 30, and X is a salt forming anion as defined above;

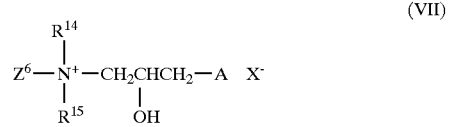

wherein $R^{14}$ and $R^{15}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

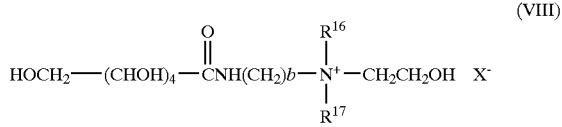

(VIII)

wherein b is 2 or 3, $R^{16}$ and $R^{17}$, independently are $C_1$–$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commerically available under the following tradenames; VARISOFT 110, VARIQUAT K1215 and 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Salts of primary, secondary, and tertiary fatty amines are also suitable cationic surfactants. The alkyl groups of such amines preferably have from about 12 to about 22 carbon atoms, and can be substituted or unsubstituted. Particularly useful are salts of amidoamines which are selected from the species disclosed above under the title "AMIDE AMINE" and "ACID". Preferably, the salts of amidoamines are used as cationic conditioning agents in the composition B.

Cationic Polymer

The cationic polymer useful herein is described below. As used herein, the term "polymer" shall include materials whether made by polymerization of one type of monomer or made by two (i.e., copolymers) or more types of monomers.

Preferably, the cationic polymer is a water-soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least about 1.1 meq/gram, still more preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

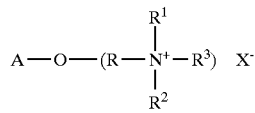

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

Low Melting Point Oil

The hair conditioning composition B of the present invention comprises a low melting point oil, which has a melting point of less than 25° C., and is included in the composition at a level by weight of from about 0.1% to about 10%, preferably from about 0.25% to about 6%.

The low melting point oil having a melting point of less than 25° C., can be also included in the composition A at a level by weight of, preferably from about 0.1% to about 10%, more preferably from about 0.25% to about 6%, still more preferably from about 0.3% to about 3%.

The low melting point oil useful herein is selected from the group consisting of hydrocarbon having from 10 to about 40 carbon atoms, unsaturated fatty alcohols having from about 10 to about 30 carbon atoms, unsaturated fatty acids having from about 10 to about 30 carbon atoms, fatty acid derivatives, fatty alcohol derivatives, ester oils, poly α-olefin oils, and mixtures thereof.

Fatty alcohols useful herein include those having from about 10 to about carbon atoms, preferably from about 12 to about 22 carbon atoms, and more preferably from about 16 to about 22 carbon atoms. These fatty alcohols are unsaturated and can be straight or branched chain alcohols. Suitable fatty alcohols include, for example, oleyl alcohol, isostearyl alcohol, tridecylalcohol, decyl tetradecyl alcohol, and octyl dodecyl alcohol. These alcohols are available, for example, from Shinnihon Rika.

Low melting point oils useful herein include pentaerythritol ester oils, trimethylol ester oils, poly α-olefin oils, citrate ester oils, glyceryl ester oils, and mixtures thereof, and the ester oil useful herein is water-insoluble. As used herein, the term "water-insoluble" means the compound is substantially not soluble in water at 25° C.; when the compound is mixed with water at a concentration by weight of above 1.0%, preferably at above 0.5%, the compound is temporarily dispersed to form an unstable colloid in water, then is quickly separated from water into two phases.

Pentaerythritol ester oils useful herein are those having the following formula:

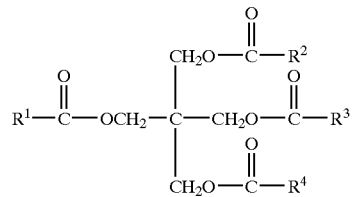

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Trimethylol ester oils useful herein are those having the following formula:

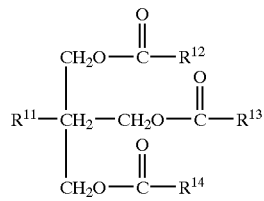

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Poly α-olefin oils useful herein are those derived from 1-alkene monomers having from about 6 to about 16 carbons, preferably from about 6 to about 12 carbons atoms. Nonlimiting examples of 1-alkene monomers useful for preparing the poly α-olefin oils include 1-hexene, 1-octene, 1-decene, 1-dodecene, 1-tetradecene, 1-hexadecene, branched isomers such as 4-methyl-1-pentene, and mixtures thereof. Preferred 1-alkene monomers useful for preparing the poly α-olefin oils are 1-octene, 1-decene, 1-dodecene, 1-tetradecene, 1-hexadecene, and mixtures thereof. Poly α-olefin oils useful herein further have a viscosity of from about 1 to about 35,000 cst, a molecular weight of from about 200 to about 60,000, and a polydispersity of no more than about 3.

Poly α-olefin oils having a molecular weight of at least about 800 are useful herein. Such high molecular weight poly α-olefin oils are believed to provide long lasting moisturized feel to the hair. Poly α-olefin oils having a molecular weight of less than about 800 are useful herein. Such low molecular weight poly α-olefin oils are believed to provide a smooth, light, clean feel to the hair.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Mobil Chemical Co.

Citrate ester oils useful herein are those having a molecular weight of at least about 500 having the following formula:

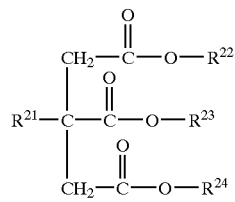

wherein $R^{21}$ is OH or $CH_3COO$, and $R^{22}$, $R^{23}$, and $R^{24}$, independently, are branched, straight, saturated, or unsaturated alkyl, aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl, aryl, and alkylaryl groups having from 8 to about 22 carbons. More preferably, $R^{21}$, $R^{22}$, $R^{23}$ and $R^{24}$ are defined so that the molecular weight of the compound is at least about 800.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Glyceryl ester oils useful herein are those having a molecular weight of at least about 500 and having the following formula:

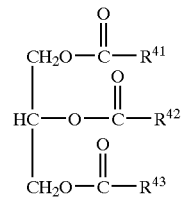

wherein $R^{41}$, $R^{42}$, and $R^{43}$, independently, are branched, straight, saturated, or unsaturated alkyl, aryl, and alkylaryl groups having from 1 to about 30 carbons. Preferably, $R^{41}$, $R^{42}$, and $R^{43}$, independently are branched, straight, saturated, or unsaturated alkyl, aryl, and alkylaryl groups having from 8 to about 22 carbons. More preferably, $R^{41}$, $R^{42}$, and $R^{43}$ are defined so that the molecular weight of the compound is at least about 800.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Silicone Compounds

Preferably, the composition A of the present invention may further comprises silicone compound. The silicone compound can be included in the composition A at a level by weight of, preferably from about 0.1% to about 10%, more preferably from about 0.25% to about 8%, still more preferably from about 0.5% to about 3%.

The silicone compound can be also included in the composition B at a level by weight of, preferably from about 0.1% to about 10%, more preferably from about 0.25% to about 8%, still more preferably from about 0.5% to about 3%.

The silicone compounds hereof can include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by conventional polymerization, or emulsion polymerization.

The silicone compounds for use herein will preferably have a viscosity of from about 1,000 to about 2,000,000 centistokes at 25° C., more preferably from about 10,000 to about 1,800,000, and even more preferably from about 25,000 to about 1,500,000. The viscosity can be measured by means of a glass capillary viscometer as set forth in Dow Corning Corporate Test Method CTM0004, Jul. 20, 1970, which is incorporated by reference herein in its entirety. Silicone compound of high molecular weight may be made by emulsion polymerization.

Silicone compounds useful herein include polyalkyl polyaryl siloxanes, polyalkyleneoxide-modified siloxanes, silicone resins, amino-substituted siloxanes, and mixtures thereof. The silicone compound is preferably selected from the group consisting of polyalkyl polyaryl siloxanes, polyalkyleneoxide-modified siloxanes, silicone resins, and mixtures thereof, and more preferably from one or more polyalkyl polyaryl siloxanes.

Polyalkyl polyaryl siloxanes useful here in include those with the following structure (I)

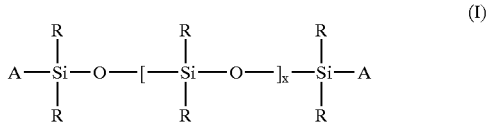

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their ViscasilR and SF 96 series, and from Dow Corning in their Dow Corning 200 series. Polymethylphenylsiloxanes, for example, from the General Electric Company as SF 1075 methyl phenyl fluid or from Dow Corning as 556 Cosmetic Grade Fluid, are useful herein.

Also preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

Another polyalkyl polyaryl siloxane that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference in, their entirety. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof.

Polyalkyleneoxide-modified siloxanes useful herein include, for example, polypropylene oxide modified and polyethylene oxide modified polydimethylsiloxane. The ethylene oxide and polypropylene oxide level should be sufficiently low so as not to interfere with the dispersibility characteristics of the silicone. These material are also known as dimethicone copolyols.

Silicone resins, which are highly crosslinked polymeric siloxane systems, are useful herein. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of tri-functional and tetra-functional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

Silicone resins can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO)_{.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Other amino-substituted siloxane which can be used are represented by the formula (V):

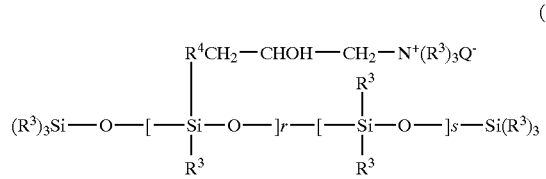

(V)

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Polypropylene Glycol

Preferably, the composition A of the present invention may further comprises a polypropylene glycol. The polypropylene glycol can be included in the composition A at a level by weight of, preferably from about 0.1% to about 10%, more preferably from about 0.25% to about 6%.

The polypropylene glycol can be also included in the composition B at a level by weight of, preferably from about 0.1% to about 10%, more preferably from about 0.25% to about 6%.

The polypropylene glycol useful herein may has a weight average molecular weight of preferably from about 200 g/mol to about 100,000 g/mol, more preferably from about 1,000 g/mol to about 60,000 g/mol. Without intending to be limited by theory, it is believed that the polypropylene glycol herein deposits onto, or is absorbed into hair to act as a moisturizer buffer, and/or provides one or more other desirable hair conditioning benefits. As used herein, the term "polypropylene glycol" includes single-polypropylene glycol-chain segment polymers, and multi-polypropylene glycol-chain segment polymers. The general structure of branched polymers such as the multi-polypropylene glycol-chain segment polymers herein are described, for example, in "Principles of Polymerization," pp. 17–19, G. Odian, (John Wiley & Sons, Inc., 3$^{rd}$ ed., 1991).

The polypropylene glycol herein are typically polydisperse polymers. The polypropylene glycols useful herein have a polydispersity of from about 1 to about 2.5, preferably from about 1 to about 2, and more preferably from about 1 to about 1.5. As used herein, the term "polydispersity" indicates the degree of the molecular weight distribution of the polymer sample. Specifically, the polydispersity is a ratio, greater than 1, equal to the weight average molecular weight divided by the number average molecular weight. For a further discussion about polydispersity, see "Principles of Polymerization," pp. 20–24, G. Odian, (John Wiley & Sons, Inc., 3$^{rd}$ ed., 1991).

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. The solubility in water of the polypropylene glycol herein may be chosen by the artisan according to a variety of factors. Accordingly, for a leave-on hair care composition, it is preferred that the polypropylene glycol herein be a water-soluble polypropylene glycol. Solubility information is readily available from polypropylene glycol suppliers, such as Sanyo Kasei (Osaka, Japan). However, the present invention may also take the form of a rinse-off hair care composition. Without intending to be limited by theory, it is believed that in such a composition, a water-soluble polypropylene glycol may be too easily washed away before it effectively deposits on hair and provides the desired benefit(s). For such a composition, a less soluble, or even a water-insoluble polypropylene glycol is therefore preferred. Accordingly, for a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

Preferably the polypropylene glycol is selected from the group consisting of a single-polypropylene glycol-chain segment polymer, a multi-polypropylene glycol-chain segment polymer, and mixtures thereof, more preferably selected from the group consisting of a single-polypropylene glycol-chain segment polymer of Formula I, below, a multi-polypropylene glycol-chain segment polymer of Formula II, below, and mixtures thereof.

Single-Polypropylene Glycol-Chain Segment Polymer

Accordingly, a highly preferred single-polypropylene glycol-chain segment polymer has the formula:

(III), wherein a is a value from about 4 to about 400, preferably from about 20 to about 100, and more preferably from about 20 to about 40.

The single-polypropylene glycol-chain segment polymer useful herein is typically inexpensive, and is readily available from, for example, Sanyo Kasei (Osaka, Japan), Dow Chemicals (Midland, Mich., USA), Calgon Chemical, Inc. (Skokie, Ill., USA), Arco Chemical Co. (Newton Square Pa., USA), Witco Chemicals Corp. (Greenwich, Conn., USA), and PPG Specialty Chemicals (Gumee, Ill., USA).

Multi-Polypropylene Glycol-Chain Segment Polymer

A highly preferred multi-polypropylene glycol-chain segment polymer has the formula:

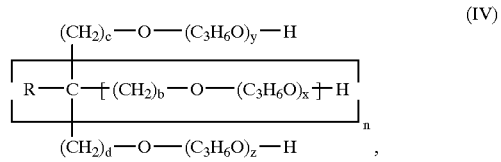

(IV)

wherein n is a value from about 0 to about 10, preferably from about 0 to about 7, and more preferably from about 1 to about 4. In Formula IV, each R" is independently selected from the group consisting of H, and $C_1$–$C_{30}$ alkyl, and preferably each R" is independently selected from the group consisting of H, and $C_1$–$C_4$ alkyl. In Formula IV, each b is independently a value from about 0 to about 2, preferably from about 0 to about 1, and more preferably b=0. Similarly, c and d are independently a value from about 0 to about 2, preferably from about 0 to about 1. However, the total of b+c+d is at least about 2, preferably the total of b+c+d is from about 2 to about 3. Each e is independently a value of 0 or 1, if n is from about 1 to about 4, then e is preferably equal to 1. Also in Formula IV, x, y, and z is independently a value of from about 1 to about 120, preferably from about 7 to about 100, and more preferably from about 7 to about 100, where x+y+z is greater than about 20.

Examples of the multi-polypropylene glycol-chain segment polymer of Formula IV which is especially useful herein includes polyoxypropylene glyceryl ether (n=1, R'=H, b=0, c and d=1, e=1, and x, y, and z independently indicate the degree of polymerization of their respective polypropylene glycol-chain segments; available as New Pol GP-4000, from Sanyo Kasei, Osaka, Japan), polypropylene trimethylol propane (n=1, R'=$C_2H_5$, b=1, c and d=1, e=1, and x, y, and z independently indicate the degree of polymerization of their respective polypropylene glycol-chain segments), polyoxypropylene sorbitol (n=4, each R'=H, b=0, c and d=1, each e=1, and y, z, and each x independently indicate the degree of polymerization of their respective polypropylene glycol-chain segments; available as New Pol SP-4000, from Sanyo Kasei, Osaka, Japan), and PPG-10 butanediol (n=0, c and d=2, and y+z=10; available as Probutyl DB-10, from Croda, Inc., of Parsippany, N.J., U.S.A.).

In a preferred embodiment, one or more of the propylene repeating groups in the polypropylene glycol is an isopropyl oxide repeating group. More preferably one or more of the propylene oxide repeating groups of the polypropylene glycol of Formula III and/or the polypropylene glycol of Formula IV is an isopropyl oxide repeating group. Even more preferably, substantially all of the propylene oxide repeating groups of the polypropylene glycol of Formula III and/or the polypropylene glycol of Formula IV are isopropyl oxide repeating groups. Accordingly, a highly preferred single-polypropylene glycol-chain segment polymer has the formula:

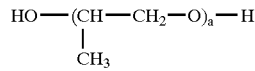

wherein a is defined as described above for Formula III. Similarly, a highly preferred multi-polypropylene glycol-chain segment polymer has the formula:

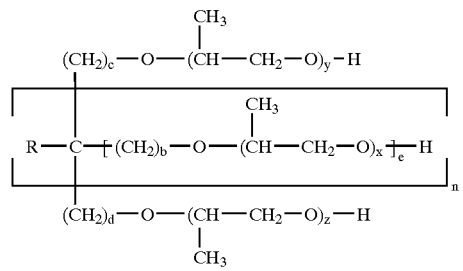

wherein n, R", b, c, d, e, x, y, and z are defined as above, for Formula IV. It is recognized that the isopropyl oxide repeating groups may also correspond either alone, or in combination with the above depicted, to:

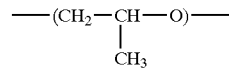

The polypropylene glycol useful herein is readily available from, for example, Sanyo Kasei (Osaka, Japan) as New pol PP-2000, New pol PP-4000, New pol GP-4000, and New pol SP-4000, from Dow Chemicals (Midland, Mich., USA), from Calgon Chemical, Inc. (Skokie, Ill., USA), from Arco Chemical Co. (Newton Square Pa., USA), from Witco Chemicals Corp. (Greenwich, Conn., USA), and from PPG Specialty Chemicals (Gumee, Ill., USA).

Polyethylene Glycol

Preferably, the composition B of present invention may further comprise a polyethylene glycol having the formula:

wherein n has an average value of from 2,000 to 14,000, preferably from about 5,000 to about 9,000, more preferably from about 6,000 to about 8,000.

The polyethylene glycol can be included in the composition B at a level by weight of, preferably from about 0.1% to about 10%, more preferably from about 0.25% to about 6%.

The polyethylene glycol can be also included in the composition A at a level by weight of, preferably from about 0.1% to about 10%, more preferably from about 0.25% to about 6%.

The polyethylene glycol described above is also known as a polyethylene oxide, and polyoxyethylene. Polyethylene glycols useful herein that are especially preferred are PEG-2M wherein n has an average value of about 2,000 (PEG-2M is also known as Polyox WSR® N-10 from Union Carbide and as PEG-2,000); PEG-5M wherein n has an average value of about 5,000 (PEG-5M is also known as Polyox WSR® N-35 and as Polyox WSR® N-80, both from Union Carbide and as PEG-5,000 and Polyethylene Glycol 300, 000); PEG-7M wherein n has an average value of about 7,000 (PEG-7M is also known as Polyox WSR® N-750 from Union Carbide); PEG-9M wherein n has an average value of about 9,000 (PEG-9M is also known as Polyox WSR® N-3333 from Union Carbide); and PEG-14M wherein n has an average value of about 14,000 (PEG-14M is also known as Polyox WSR® N-3000 from Union Carbide).

Sensates

The hair conditioning compositions A and B of the present invention may further comprise a sensate. As used herein the term "sensate" means a substance that, when applied to the skin, causes a perceived sensation of a change in conditions, for example, but not limited to, heating, cooling, refreshing and the like.

Sensates are preferably utilized at levels of from about 0.001% to about 10%, more preferably from about 0.005% to about 5%, even more preferably from about 0.01% to about 1%, by weight, of the total compositions.

Any sensate suitable for use in hair care compositions may be used herein. A non-limiting, exemplary list of suitable sensates can be found in GB-B-1315626, GB-B-1404596 and GB-B-1411785, all incorporated by reference herein. Preferred sensates for use in the compositions herein are camphor, menthol, 1-isopulegol, ethyl menthane carboxamide and trimethyl isopropyl butanamide.

Compositions

In one preferred embodiment of the present invention, the composition comprises by weight:
(a) from about 0.1% to about 15%, preferably from about 1% to about 10% of a high melting point fatty compound, preferably, the high melting point fatty compound selected from the group consisting of cetyl alcohol, stearyl alcohol, behenyl alcohol, and mixtures thereof;
(b) from about 0.1% to about 10%, preferably from about 0.5% to about 3% of an amidoamine having the following general formula:

$R^1CONH(CH_2)_m N(R^2)_2$ wherein $R^1$ is a residue of $C_{11}$ to $C_{24}$ fatty acids, $R^2$ is a $C_1$ to $C_4$ alkyl, and m is an integer from 1 to 4, preferably, the amidoamine selected from the group consisting of stearamidopropyl dimethylamine, stearamidoethyl diethylamine, and mixtures thereof;
(c) an acid selected from the group consisting of l-glutamic acid, lactic acid, hydrochloric acid, malic acid, succinic acid, acetic acid, fumaric acid, l-glutamic acid hydrochloride, tartaric acid, and mixtures thereof, at a level such that the mole ratio of amidoamine to acid is from about 1:0.3 to about 1:1, preferably, l-Glutamic acid at a level such that the mole ratio of amidoamine to acid is from about 1:0.5 to about 1:0.9;
(d) a safe and effective amount of an antidandruff agent, preferably, from about 0.3% to about 1% of zinc pyrithione;
(e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben; and
(f) an aqueous carrier;
wherein the hair conditioning composition is substantially free of the group selected from a chelating agent, methylchloroisothiazolinone, and methylisothiazolinone.

This composition may further contain a silicone compound at a level by weight of from about 0.1% to about 10%, and a sensate at a level by weight of from about 0.001% to about 10%.

In another preferred embodiment of the present invention, the composition comprises by weight:
(a) from about 0.1% to about 15%, preferably from about 1% to about 10% of a high melting point fatty compound having a melting point of 25° C. or higher,
(b) from about 0.1% to about 10%, preferably from about 0.25% to about 5% of a cationic conditioning agent;
(c) a safe and effective amount of an antidandruff agent, preferably, from about 0.3% to about 1% of zinc pyrithione;
(d) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben;
(e) an aqueous carrier; and
(f) from about 0.1% to about 10%, preferably from about 0.25% to about 6% of a polypropylene glycol,
wherein the hair conditioning composition is substantially free of the group selected from a chelating agent, methylchloroisothiazolinone, and methylisothiazolinone.

This composition may further contain a low melting point oil having a melting point of less than 25° C. at a level by weight of from about 0.1% to about 10%, preferably from about 0.25% to about 6%, more preferably from about 0.3% to about 3%, and a sensate at a level by weight of from about 0.001% to about 10%.

In another preferred embodiment of the present invention, the composition comprises by weight:
(a) from about 0.1% to about 15%, preferably from about 0.25% to about 5% of a high melting point fatty compound having a melting point of 25° C. or higher,
(b) from about 0.1% to about 10%, preferably from about 0.25% to about 5% of a cationic conditioning agent;
(c) from about 0.1% to about 10%, preferably from about 0.25% to about 6% of a low melting point oil having a melting point of less than 25° C., preferably, the low melting point oil being an unsaturated oil;
(d) a safe and effective amount of an antidandruff agent, preferably, from about 0.3% to about 1% of zinc pyrithione;
(e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben;
(f) an aqueous carrier; and
(g) from about 0.1% to about 10%, preferably from about 0.25% to about 6% of a polyethylene glycol,
wherein the hair conditioning composition is substantially free of the group selected from a chelating agent, methylchloroisothiazolinone, and methylisothiazolinone.

This composition may further contain a sensate at a level by weight of from about 0.001% to about 10%.

Additional Components

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, a mixture of Polysorbate 60 and Cetearyl Alcohol with tradename Polawax NF available from Croda Chemicals, glycerylmonostearate available from Stepan Chemicals, hydroxyethyl cellulose available from Aqualon, 3-pyridinecarboxy acid amide (niacinamide), hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate; and optical brighteners, for example polystyrylstilbenes, triazinstilbenes, hydroxycoumarins, aminocoumarins, triazoles, pyrazolines, oxazoles, pyrenes, porphyrins, imidazoles, and mixtures thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

The compositions of the present invention are suitable for rinse-off products and leave-on products, and are particularly useful for making products in the form of emulsion, cream, gel, spray or, mousse.

| | Compositions | | |
|---|---|---|---|
| Components | Example 1 | Example 2 | Example 3 |
| Cetyl Alcohol *1 | 2.0 | 2.5 | 2.0 |
| Stearyl Alcohol *2 | 3.6 | 4.5 | 3.6 |
| Stearamidopropyl Dimethylamine *3 | 1.6 | 2.0 | 1.6 |
| l-Glutamic acid *4 | 0.512 | 0.64 | 0.512 |
| Zinc pyrithione *5 | 2.0 | 2.0 | 2.0 |
| Benzyl alcohol | 0.4 | 0.4 | 0.4 |
| Phenoxy Ethanol | 0.3 | 0.3 | 0.3 |
| Methyl Paraben | 0.2 | 0.2 | 0.2 |
| Propyl Paraben | 0.1 | 0.1 | 0.1 |
| Silicone Blend *6 | 3.36 | 4.37 | 3.36 |
| Natural Menthol *19 | — | — | 0.4 |
| Perfume | 0.4 | 0.4 | 0.4 |
| 3-pyridinecarboxy acid amide | 0.05 | 0.05 | 0.05 |
| dl-Alpha tocopherol acetate | 0.05 | 0.05 | 0.05 |
| Hydrolyzed collagen *7 | 0.01 | 0.01 | 0.01 |
| Panthenol *8 | 0.05 | 0.05 | 0.05 |
| Panthenyl Ethyl Ether *9 | 0.05 | 0.05 | 0.05 |
| Octyl methoxycinnamate | 0.09 | 0.09 | 0.09 |
| Benzophenone-3 | 0.09 | 0.09 | 0.09 |
| Citric Acid | amount necessary to adjust pH 3–7 | | |
| Deionized Water | q.s. to 100% | | |
| Components | Example 4 | Example 5 | Example 6 |
| Cetyl Alcohol *1 | 2.6 | 2.0 | 2.6 |
| Stearyl Alcohol *2 | 4.6 | 3.6 | 4.6 |
| Stearamidopropyl Dimethylamine *3 | 1.8 | 1.6 | 1.8 |
| l-Glutamic acid *4 | 0.6 | 0.5 | 0.6 |
| Pentaerythritol Tetraisostearate *11 | 1.0 | 0.5 | 1.0 |
| Polypropylene Glycol *18 | 4.5 | 4.0 | 4.5 |
| Zinc pyrithione *5 | 2.0 | 2.0 | 2.0 |
| Benzyl alcohol | 0.4 | 0.4 | 0.4 |
| Phenoxy Ethanol | 0.3 | 0.3 | 0.3 |
| Methyl Paraben | 0.2 | 0.2 | 0.2 |
| Propyl Paraben | 0.1 | 0.1 | 0.1 |
| Natural Menthol *19 | — | — | 0.4 |
| Perfume | 0.4 | 0.4 | 0.4 |
| 3-pyridinecarboxy acid amide | 0.05 | 0.05 | 0.05 |
| dl-Alpha tocopherol acetate | 0.05 | 0.05 | 0.05 |
| Hydrolyzed collagen *7 | 0.01 | 0.01 | 0.01 |
| Panthenol *8 | 0.05 | 0.05 | 0.05 |
| Panthenyl Ethyl Ether *9 | 0.05 | 0.05 | 0.05 |
| Octyl methoxycinnamate | 0.09 | 0.09 | 0.09 |
| Benzophenone-3 | 0.09 | 0.09 | 0.09 |
| Citric Acid | amount necessary to adjust pH 3–7 | | |
| Deionized Water | q.s. to 100% | | |
| Components | Example 7 | Example 8 | Example 9 |
| Cetyl Alcohol *1 | 0.96 | 1.2 | 0.96 |
| Stearyl Alcohol *2 | 0.64 | 0.8 | 0.64 |
| Stearamidopropyl Dimethylamine *3 | 1.0 | | 1.0 |
| Ditallow dimethyl ammonium chloride *10 | 0.75 | 0.64 | 0.75 |
| Pentaerythritol Tetraisostearate *11 | 0.5 | | 0.5 |
| Pentaerythritol Tetraoleate *12 | | 0.2 | |
| Oleyl alcohol *13 | | 0.25 | |

| -continued | | | |
|---|---|---|---|
| | Compositions | | |
| Trimethylolpropane Triisostearate *14 | | 0.25 | |
| PEG 2M *15 | 0.5 | 0.5 | 0.5 |
| Polysorbate 60 *16 | 0.25 | 0.25 | 0.25 |
| Cetearyl Alcohol *16 | 0.25 | 0.25 | 0.25 |
| Glycerylmonostearate *17 | 0.25 | 0.25 | 0.25 |
| Zinc pyrithione *5 | 2.0 | 2.0 | 2.0 |
| Benzyl alcohol | 0.4 | 0.4 | 0.4 |
| Phenoxy Ethanol | 0.3 | 0.3 | 0.3 |
| Methyl Paraben | 0.2 | 0.2 | 0.2 |
| Propyl Paraben | 0.1 | 0.1 | 0.1 |
| Natural Menthol *19 | — | — | 0.4 |
| Perfume | 0.4 | 0.4 | 0.4 |
| 3-pyridinecarboxy acid amide | 0.05 | 0.05 | 0.05 |
| dl-Alpha tocopherol acetate | 0.05 | 0.05 | 0.05 |
| Hydrolyzed collagen *7 | 0.01 | 0.01 | 0.01 |
| Panthenol *8 | 0.05 | 0.05 | 0.05 |
| Panthenyl Ethyl Ether *9 | 0.05 | 0.05 | 0.05 |
| Octyl methoxycinnamate | 0.09 | 0.09 | 0.09 |
| Benzophenone-3 | 0.09 | 0.09 | 0.09 |
| Citric Acid | amount necessary to adjust pH 3–7 | | |
| Deionized Water | q.s. to 100% | | |

Definitions of Components

*1 Cetyl Alcohol: Konol series available from Shin Nihon Rika.

*2 Stearyl Alcohol: Konol series available from Shin Nihon Rika.

*3 Stearamidopropyl Dimethylamine: SAPDMA available from Inolex.

*4 l-Glutamic acid: l-Glutamic acid (cosmetic grade) available from Ajinomoto.

*5 Zinc pyrithinone: Zinc pyrithione U/2 available from Olin

*6 Silicone Blend: SE 76 available from General Electric

*7 Hydrolyzed collagen: Peptein 2000 available from Hormel.

*8 Panthenol: available from Roche.

*9 Panthenyl Ethyl Ether: available from Roche.

*10 Ditallow dimethyl ammonium chloride: Available from Witco Chemicals.

*11 Pentaerythritol Tetraisostearate: KAK PTI obtained by Kokyu alcohol.

*12 Pentaerythritol Tetraoleate: Available from Shin Nihon-Rika.

*13 Oleyl alcohol: Available from New Japan Chemical.

*14 Trimethylolpropane Triisostearate: KAK TTI obtained by Kokyu alcohol.

*15 PEG-2M: Polyox obtained by Union Carbide.

*16 Polysorbate 60, Cetearyl Alcohol: mixture sold as Polawax NF obtained by Croda Chemicals.

*17 Glycerylmonostearate: Available from Stepan Chemicals.

*18 Polypropylene Glycol: PP2000 available from Sanyo Kasei.

*19 Natural Menthol: Menthol Crystal available from Dr Kolb.

Method of Preparation

The hair conditioning compositions of Examples 1 and 9 as shown above can be prepared by any conventional method well known in the art. They are suitably made as follows: when included in the composition, polymeric materials such as polypropylene glycol are dispersed in water at room temperature to make a polymer solution, and heated up to above 70° C. Amidoamine and acid, and when present, other cationic surfactants, ester oil of low melting point oil are added in the solution with agitation. Then high melting point fatty compound, and when present, other low melting point oils and benzyl alcohol are also added in the solution with agitation. The mixture thus obtained is cooled down to below 60° C., and the remaining components such as zinc pyrithione, silicone compound, and menthol are added with agitation, and further cooled down to about 30° C.

A triblender and/or mill can be used in each step, if necessary to disperse the materials.

Alternatively, up to 50% of the acid can be added after cooling below 60° C.

The embodiments disclosed herein have many advantages. For example, they can provide effective antidandruff efficacy, while not deteriorating conditioning benefits such as wet hair feel, spreadability, and rinsability, as well as providing glossiness, and dry combing.

It is understood that the examples and embodiments described herein are for illustrative purposes only and that various modifications or changes in light thereof will be suggested to one skilled in the art without departing from its spirit and scope.

What is claimed is:

1. A hair conditioning composition comprising by weight:
   (a) from about 0.1% to about 15% of a high melting point fatty compound;
   (b) from about 0.1% to about 10% of an amidoamine having the following general formula:

wherein $R^1$ is a residue of $C_{11}$ to $C_{24}$ fatty acids, $R^2$ is a $C_1$ to $C_4$ allyl, and m is an integer from 1 to 4;
   (c) an acid selected from the group consisting of l-glutamic acid, lactic acid, hydrochloric acid, malic acid, succinic acid, acetic acid, fumaric acid, l-glutamic acid hydrochloride, tartaric acid, and mixtures thereof, at a level such that the mole ratio of amidoamine to acid is from about 1:0.3 to about 1:1;
   (d) a safe and effective amount of an antidandruff agent;
   (e) a preservative system comprising by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben; and
   (f) an aqueous carrier;
wherein the hair conditioning composition is substantially free of the group selected from a chelating agent, methylchloroisothiazolinone, and methylisothiazolinone.

2. The hair conditioning composition according to claim 1 further comprising a silicone compound.

3. The hair conditioning composition according to claim 1 further comprising by weight from about 0.1% to about 10% of a polypropylene glycol.

4. The hair conditioning composition according to claim 1 comprising by weight:
   (a) from about 1% to about 10% of the high melting point fatty compound selected from the group consisting of cetyl alcohol, stearyl alcohol, behenyl alcohol, and mixtures thereof;
   (b) from about 0.5% to about 3% of the amidoamine selected from the group consisting of stearamidopropyl dimethylamine, stearamidoethyl diethylamine, and mixtures thereof;
   (c) l-glutamic acid at a level such that the mole ratio of amidoamine to acid is from about 1:0.5 to about 1:0.9, and
   (d) from about 0.3% to about 1% of zinc pyrithione.

5. The hair conditioning composition according to claim 1 further comprising by weight from about 0.001% to about 10% of a sensate.

6. A hair conditioning composition comprising by weight:
   (a) from about 0.1% to about 15% of a high melting point fatty compound having a melting point of 25° C. or higher;
   (b) from about 0.1% to about 10% of a cationic conditioning agent;
   c) from about 0.1% to about 10% of a low melting point oil having a melting point of less than 25° C.;
   (d) a safe and effective amount of an antidandruff agent;
   (e) a preservative system comprising, by weight of the entire composition, from about 0.1% to about 1.0% of benzyl alcohol, from about 0.1% to about 1.0% of phenoxy ethanol, from about 0.05% to about 1.0% of methyl paraben, and from about 0.01% to about 1.0% of propyl paraben; and
   (f) an aqueous carrier;
wherein the hair conditioning composition is substantially free of the group selected from a chelating agent, methylchloroisothiazolinone, and methylisothiazolinone.

7. The hair conditioning composition according to claim 6 wherein the low melting point oil is an unsaturated fatty alcohol.

8. The hair conditioning composition according to claim 7 wherein the low melting point oil is selected from the group consisting of:
   (a) pentaerythritol ester oils having a molecular weight of at least about 800, and having the following formula:

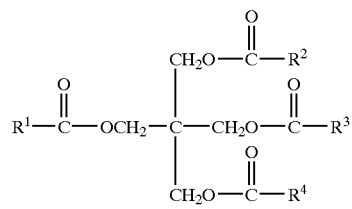

wherein R1, R2, R3, and R4, independently, are branched, straight, saturated, or unsaturated alkyl, aryl, and alkylaryl groups having from 1 to about 30 carbons;
   (b) trimethylol ester oils having a molecular weight of at least about 800, and having the following formula:

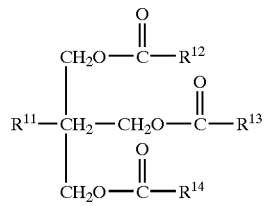

wherein R11 is an alkyl group having from 1 to about 30 carbons, and R12, R13, and R14, independently, are branched, straight, saturated, or unsaturated alkyl, aryl, and alkylaryl groups having from 1 to about 30 carbons;

(c) poly α-olefin oils derived from 1-alkene monomers having from about 6 to about 16 carbons, the poly α-olefin oils having a viscosity of from about 1 to about 35,000 cst, a molecular weight of from about 200 to about 60,000, and a polydispersity of no more than about 3;

(d) citrate ester oils having a molecular weight of at least about 500, and having the following formula:

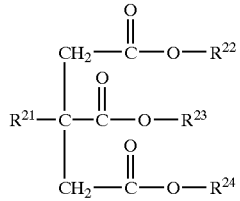

wherein R21 is OH or CH3COO, and R22, R23, and R24, independently, are branched, straight, saturated, or unsaturated alkyl, aryl, and alkylaryl groups having from 1 to about 30 carbons;

(e) glyceryl ester oils having a molecular weight of at least about 500, and having the following formula:

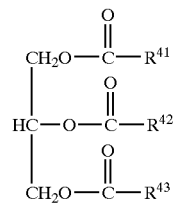

wherein R41, R42, and R43, independently, are branched, straight, saturated, or unsaturated alkyl, aryl, and alkylaryl groups having from 1 to about 30 carbons;

and mixtures thereof.

9. The hair conditioning composition according to claim 6 further comprising by weight from about 0.1% to about 10% of a polyethylene glycol having the formula:

H(OCH2CH2)n-OH wherein n has an average value of from 2,000 to 14,000.

10. The hair conditioning composition according to claim 9 further comprising by weight from about 0.001% to about 10% of a sensate.

* * * * *